(12) United States Patent
Öhlander et al.

(10) Patent No.: US 8,790,254 B2
(45) Date of Patent: Jul. 29, 2014

(54) MEDICAL DEVICE FOR DETERMINING THE POSTURE OF PATIENT

(75) Inventors: Malin Öhlander, Stockholm (SE); Nils Holmström, Järfälla (SE); Kjell Norén, Solna (SE)

(73) Assignee: St. Jude Medical AB, Jarfalla (SE)

( * ) Notice: Subject to any disclaimer, the term of this patent is extended or adjusted under 35 U.S.C. 154(b) by 1890 days.

(21) Appl. No.: 11/993,254

(22) PCT Filed: Jun. 29, 2005

(86) PCT No.: PCT/SE2005/001030
§ 371 (c)(1),
(2), (4) Date: Jan. 22, 2010

(87) PCT Pub. No.: WO2007/001219
PCT Pub. Date: Jan. 4, 2007

(65) Prior Publication Data
US 2010/0113961 A1    May 6, 2010

(51) Int. Cl.
*A61B 5/00* (2006.01)
*G06F 19/00* (2011.01)
*A61B 5/053* (2006.01)

(52) U.S. Cl.
CPC *G06F 19/34* (2013.01); *A61B 5/053* (2013.01)
USPC ...................................................... 600/300

(58) Field of Classification Search
USPC .................... 600/300, 301, 534, 537; 607/17
See application file for complete search history.

(56) References Cited

U.S. PATENT DOCUMENTS

| | | | |
|---|---|---|---|
| 5,233,984 A | | 8/1993 | Thompson |
| 5,865,760 A | * | 2/1999 | Lidman et al. ................ 600/509 |
| 5,876,353 A | * | 3/1999 | Riff .............................. 600/547 |
| 5,957,861 A | | 9/1999 | Combs et al. |
| 6,104,949 A | * | 8/2000 | Pitts Crick et al. ........... 600/547 |

(Continued)

FOREIGN PATENT DOCUMENTS

| | | |
|---|---|---|
| EP | 0 985 429 A2 | 3/2000 |
| EP | 1 338 246 A1 | 8/2003 |

OTHER PUBLICATIONS

"Errors in Prolonged Electrical Impedance Measurements Due to Electrode Repositioning and Postural Changes," Lozano et al., Physiol. Meas. 16 (1995), pp. 121-130.

*Primary Examiner* — Gary Jackson
*Assistant Examiner* — Bobby Soriano

(57) ABSTRACT

In a method and a device for determining the posture of a patient, a bio-impedance measurement device, having a number of electrodes configured to interact with the patient in a number of different electrode configurations, is operated to initiate a patient posture determining session by measuring an impedance value of the patient with the electrodes in at least one configuration among the number of configurations. A reference impedance value from among a number of stored reference impedance values for the at least one configuration is selected. The number of stored reference impedance values are respectively associated with different postures of the patient, and the posture associated with the selected reference impedance value represents a candidate posture. The measured impedance value is compared with the selected reference impedance value, thereby obtaining a comparison result. Dependent on said comparison result, it is automatically determined whether the current posture of the patient conforms to the candidate posture.

23 Claims, 8 Drawing Sheets

(56) References Cited

U.S. PATENT DOCUMENTS

| | | | |
|---|---|---|---|
| 6,122,042 A * | 9/2000 | Wunderman et al. | 356/73 |
| 6,600,949 B1 * | 7/2003 | Turcott | 600/518 |
| 6,980,853 B2 * | 12/2005 | Miyoshi et al. | 600/547 |
| 7,226,422 B2 * | 6/2007 | Hatlestsad et al. | 600/534 |
| 7,387,610 B2 * | 6/2008 | Stahmann et al. | 600/538 |
| 7,430,447 B2 * | 9/2008 | Min et al. | 607/17 |
| 7,502,649 B2 * | 3/2009 | Ben-Haim et al. | 607/40 |
| 7,515,961 B2 * | 4/2009 | Germanson et al. | 607/27 |
| 7,603,170 B2 * | 10/2009 | Hatlestad et al. | 600/547 |
| 7,907,997 B2 * | 3/2011 | Stahmann et al. | 600/547 |
| 7,986,994 B2 * | 7/2011 | Stadler et al. | 607/17 |
| 8,137,270 B2 * | 3/2012 | Keenan et al. | 600/301 |
| 2001/0007055 A1 * | 7/2001 | Fukuda | 600/547 |
| 2003/0023184 A1 * | 1/2003 | Pitts-Crick et al. | 600/547 |
| 2003/0100925 A1 * | 5/2003 | Pape et al. | 607/17 |
| 2004/0054298 A1 * | 3/2004 | Masuo et al. | 600/547 |
| 2004/0073093 A1 * | 4/2004 | Hatlestad | 600/300 |
| 2004/0102712 A1 | 5/2004 | Belalcazar et al. | |
| 2004/0210157 A1 * | 10/2004 | Organ et al. | 600/547 |
| 2005/0090760 A1 * | 4/2005 | Kobayashi | 600/547 |
| 2005/0148897 A1 * | 7/2005 | Cho et al. | 600/533 |
| 2005/0234518 A1 * | 10/2005 | Heruth et al. | 607/6 |
| 2006/0025699 A1 * | 2/2006 | Maile et al. | 600/528 |
| 2006/0041280 A1 * | 2/2006 | Stahmann et al. | 607/17 |
| 2006/0241512 A1 * | 10/2006 | Kwok et al. | 600/547 |
| 2006/0241513 A1 * | 10/2006 | Hatlestad et al. | 600/547 |
| 2006/0258952 A1 * | 11/2006 | Stahmann et al. | 600/547 |
| 2006/0264776 A1 * | 11/2006 | Stahmann et al. | 600/547 |
| 2006/0293609 A1 * | 12/2006 | Stahmann et al. | 600/547 |
| 2007/0179556 A1 * | 8/2007 | Ben Haim et al. | 607/40 |

* cited by examiner

MEDICAL DEVICE FOR DETERMINING THE POSTURE OF PATIENT

BACKGROUND OF THE INVENTION

1. Field of the Invention

The present invention generally relates to implantable medical devices, such as cardiac pacemakers and implantable cardioverter/defibrillators, and in particular to a method, a medical device, a computer program product and a computer readable medium for determining the posture of a patient.

2. Description of the Prior Art

A severe problem associated with measurement of, inter glia, the blood pressure of the chambers, contractility, endocardial acceleration, blood flow, coronary blood flow, the sinus rate, the electrical bio-impedance, such as the thoracic impedance and the cardiogenic impedance is that the accurateness and reliability, and, hence the repeatability, of the obtained signals are greatly affected by factors like the body position of the patient, patient activity levels, heart rate frequency, etc. In particular, it has been found that the body position of the patient is of major importance with regard to the blood pressure of the chambers, contractility, endocardial acceleration, blood flow, coronary blood flow, the sinus rate, the electrical bio-impedance, such as the thoracic impedance and the cardiogenic impedance, etc. Repeatable measurements of such parameters are of a great value for identifying changes of many different conditions in the body of a patient. For example, for many algorithms it is important to know the position or posture of the patient to be able to compare obtained data to data recorded previously, for example at pulmonary edema monitoring, measurements of electrical bio-impedance (e.g. cardiac impedance) in order to calculate trends on how a patient's disease progresses or on how a certain condition progresses in a accurate and reliable way. Electrical bio-impedance signals have, for example, been found to constitute an effective measure for identifying changes of many different conditions in the body of a patient, such as incipient pulmonary edema and the progression of pulmonary edema due to CHF, i.e. the accumulation of fluids in the lung-region associated with pulmonary edema affects the thoracic impedance, or more specifically the DC impedance level, since the resistivity of the lung changes in accordance with a change of the ratio of fluid to air.

Clinical and pre-clinical measurements have, in fact, shown that the electrical bio-impedance is dependent to a significant extent also regarding different positions even when the patient is lying down, for example, whether the patient is lying on a side or is lying on the back. Regarding impedance measurements, a major reason for this is that the measurement depends on the measurement vector, i.e. the vector between the nodes that the current is applied between and the vector the voltage is measured between. When the body shifts position, these vectors will change since the gravity will influence, for example, tissue between the nodes and how it moves. This significant posture dependence applies both when looking at the morphology of the impedance signal in general and the DC-levels of the impedance signal. Pre-clinical trials on sheep have shown that the DC-level of the impedance may vary as much as 25-40% depending on the subject's posture: This is true for both the thoracic impedance, for example, measured over the lungs (for example between a case of an implantable device and an electrode placed within the heart) and the cardiogenic impedance, for example the DC impedance measured within the heart (for example RV-RA or RV-LV).

Accordingly, there is a need for a method and medical device that are capable of determining the posture of a patient in an accurate and reliable way.

SUMMARY OF THE INVENTION

Thus, an object of the present invention is to provide a method and medical device that are capable of determining the present posture of a patient in an accurate and reliable way.

As used herein, the term "impedance" refers to the DC component of the impedance. The measured impedance consists of a DC component and an AC component, where the DC component is the baseline around which the AC component fluctuates. The DC component reflects the amount of tissue and fluids that are located between the measuring points that the impedance is measured in-between and the AC components reflects how respiration and cardiac activity influence the impedance signal. Hence, the term "impedance value" corresponds to the DC impedance level.

As used herein, the term "intra thoracic impedance" refers to an impedance measurement over the thorax by using an implantable medical device, i.e. an impedance measurement where the impedance measurement vector spans over the thorax.

Moreover, the term "cardiogenic impedance" as used herein the impedance or resistance variation that origins from cardiac contractions.

According to the present invention, a method for determining the posture of a patient includes initiating a patient posture determining session by performing an electrical bio-impedance measurement session in at least one of a number of different electrode configurations in order to measure an impedance value, i.e. the DC impedance level, for the at least one configuration, obtaining or reading reference impedance values stored in advance for the at least one configuration and for at least one potential posture of the patient, comparing the measured impedance value for the at least one configuration with corresponding stored reference impedance values for at least one potential posture of the patient, and determining the present posture of the patient by using results from the comparison between measured impedance values and the stored reference impedance values.

According to the present invention, a medical device is provided for determining the posture of a patient, the device being connectable to a patient in a number of different electrode configurations. The medical device according to the present invention has an impedance measuring arrangement for measuring an electrical bio-impedance at each of the number of electrode configurations, the impedance measuring arrangement, upon receiving a triggering signal, initiating a patient posture determining session by performing an impedance measurement session in at least one of the electrode configurations in order to measure an impedance value for the at least one configuration. A processor obtains or reads reference impedance values stored in advance in a storage unit for the at least one configuration and for at least one potential posture of the patient, and compares the measured impedance values with corresponding stored reference impedance values for at least one potential posture of the patient. The processor determines the present posture of the patient by using results from the comparison between measured impedance values and the stored reference impedance values.

According to the present invention, there is also provided a computer readable medium embodying instructions for causing a computer to perform a method according to the present invention.

Thus, the invention is based on the insight that the significant impedance variance between different postures of a subject and different electrode configurations for performing the impedance measurements within the subject in fact can be used to determine the present posture of the subject. The invention utilizes the findings of clinical and pre-clinical measurements showing that the electrical bio-impedance is posture dependent to a great extent also regarding different positions or postures even when the patient is lying down, for example, whether the patient is lying on a side or is lying on the back. According to the invention, the present impedance, which preferably is the DC impedance, of the patient is measured in at least one electrode configuration and compared with corresponding reference impedance values of a reference impedance matrix. The result from the comparison is used to determine the present posture of the patient. Consequently, variations of the DC impedance values of the patient are used to identify the present posture.

This invention provides several advantages. For example, one advantage is that reliable and accurate determinations of the posture of the patient can be achieved. These, in turn, can be used to, for example, obtain repeatable measurements of parameters such as blood pressure of the chambers, contractility, endocardial acceleration, blood flow, coronary blood flow, the sinus rate, the electrical bio-impedance, such as the thoracic impedance and the cardiogenic impedance. Repeatable measurements of such parameters are of a great value for identifying changes of many different conditions in the body of a patient. For example, for many algorithms it is important to know the position or posture of the patient to be able to compare obtained data to data recorded previously, for example at pulmonary edema monitoring, measurements of electrical bio-impedance (e.g. cardiac impedance) in order to calculate trends on how a patient's disease progresses or on how a certain condition progresses in a accurate and reliable way. Electrical bio-impedance signals have, for example, been found to constitute an effective measure for identifying changes of many different conditions in the body of a patient, such as incipient pulmonary edema and the progression of pulmonary edema due to CHF. Another advantage is that the method and device for determining the posture of the patient is customized to the specific patient. A conventional position sensor cannot be adapted to a specific patient in such a convenient and efficient way. Yet another advantage is that the need of an additional position sensor in the implantable device is removed.

According to an embodiment of the present invention, at least one reference impedance value is obtained for each of a predetermined number of electrode configurations and each of a predetermined number of postures, which at least one value is stored the reference value matrix, thus containing reference impedance values for each electrode configuration and each potential posture. This training of the device may be performed at a doctor's office, where the patient, under the doctor's supervision, is instructed to change his or her posture to a number of predetermined distinct postures. In each posture an impedance value is measured for each electrode configuration and is stored as a reference impedance value in the reference matrix. Alternatively, the patient may perform this training in accordance with, for example, written instructions, and, hence, the assistance of a doctor or any hospital stuff is not required in this case.

In another embodiment of the present invention, it is checked whether a difference between the measured impedance value for the at least one configuration and the corresponding stored reference impedance values is within a predetermined interval; and if the difference is identified to be outside the interval at a predetermined number of posture determining sessions, the reference impedance values are updated by using the measured impedance values. Preferably, the measured impedance values from the latest posture determining session are used to replace the former reference values in order to update the reference matrix. In another embodiment, a mean value of the impedance values of the predetermined number of posture determining sessions is calculated and used to update the reference matrix. In yet another embodiment, a weighted average value of the impedance values of the predetermined number of posture determining sessions is calculated and used to update the reference matrix. In still another embodiment, a moving average of the impedance values of the predetermined number of posture determining sessions is calculated and used to update the reference matrix.

In a preferred embodiment of the present invention, each impedance value is calculated as a mean value of the measured impedance signal over a predetermined period of time. Alternatively, the breathing rate of the patient is sensed. This sensed rate can be used, for example, to calculate each measured impedance value as a mean value of the measured impedance signal over a predetermined number of breaths. In another embodiment, the measurements are synchronized with the breathing cycle of the patient and each impedance value is calculated as a mean value of the measured impedance signal over a predetermined number of breathing cycles. Hence, the accuracy of the impedance signals can be further increased.

According to embodiments of the present invention, a deviation factor is calculated for the at least one potential posture by using corresponding measured impedance values and stored reference impedance values, which deviation factor for the at least one potential posture is used to determine the present posture. According to one embodiment, the deviation factor is the squared difference sum of the measured impedance values and corresponding stored reference impedance values for at least one potential posture and the potential posture of the at least one potential postures having the lowest squared difference sum is identified. This posture is determined to be the actual or present posture of the patient.

In another embodiment of the present invention, it is checked whether the squared difference for the at least one potential posture is within a predetermined interval and the present posture of patient is determined to be the potential posture having a squared difference sum within the predetermined interval. That is, during the comparison procedure is checked whether each respective measured impedance value is within the interval for each respective reference value of each potential posture. The potential posture where all measured impedance values is within respective interval is determined to be the present posture of the patient.

According to an alternative, the heart rate of the patient is sensed, it is determined whether the heart rate is within a predetermined heart rate interval, and the patient posture determining session is initiated if the sensed heart rate is within the predetermined heart rate interval. Consequently, the position determination is not performed if the heart rate has increased above a predetermined upper limit of the interval or if the heart rate has decreased below a predetermined lower limit since it may indicate, for example, that the patient is moving too much or suffering from an infection, which, in turn, may affect the impedance measurements. Moreover, the procedure for determining the posture of the patient can be customized and adjusted to the needs and life pattern of the specific patient. Hence, the accuracy and reliability of the position determination can be further improved.

In an alternative embodiment of the present invention, an activity level of the patient is sensed, it is determined whether the sensed activity level is below a predetermined activity level; and the patient posture determining session is initiated if said sensed activity level is below said predetermined activity level. Thus, the positions or posture determination is only performed if the patient is not moving overly much since such an event may affect the measurements. This feature also allows a posture detection procedure adjusted to the specific patient. Thereby, the accuracy and reliability of the posture determination can be further improved.

In yet another embodiment of the present invention, the body temperature of the patient is sensed, and it is determined whether the temperature is within a predetermined temperature level interval and the patient posture determining session is initiated if said sensed body temperature is within said predetermined temperature level interval. Thus, it is assured that the body temperature of the patient is within a predetermined range during the posture determination. This entails the procedure for determining the posture of the patient can be customized to a higher extent. Thereby, the accuracy and reliability of the position determination can be further improved since an increased or decreased temperature may affect the measurements.

Alternatively, signals related to heart pumping activity of the patient are sensed, the cardiac output based on the signals is determined, it is determined whether the cardiac output is within a predetermined cardiac output level interval; and the patient posture determining session is initiated if the sensed cardiac output is within the predetermined cardiac output level interval. Moreover, the procedure for determining the posture of the patient can be customized and adjusted to the needs and life pattern of the specific patient. Thereby, the accuracy and reliability of the position determination can be improved.

Preferably, an updating indication signal indicating that the reference impedance values require an updating is initiated if a posture not has been determined in a patient posture determining session during a predetermined period of time. This may be the case if the patient has lost or gained weight, especially around the thorax since the new/lost tissue will cause changes in the pressure the tissue surrounding the heart will put on the heart in different positions and, thus, affecting the DC levels of the impedance.

In an alternative embodiment, the patient posture determining session can be initiated at a certain point of time during the day. In other words, it is possible to correlate the patient posture determining session with a suitable point of time during the day, for example, during the night when the activity of patient may be lower.

The methods of the present invention, as well as preferred embodiments thereof, are suitable to realize as a computer program or a computer readable medium.

DESCRIPTION OF THE PREFERRED EMBODIMENTS

Figure 1:
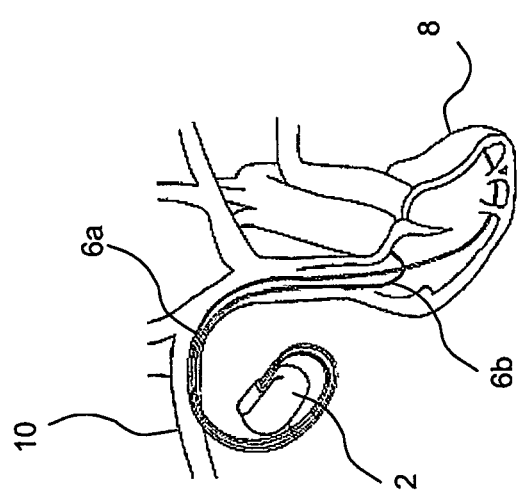
FIG. 1 is schematic diagram showing a medical device implanted in a patient in which device the present invention can be implemented.
Figure 2:
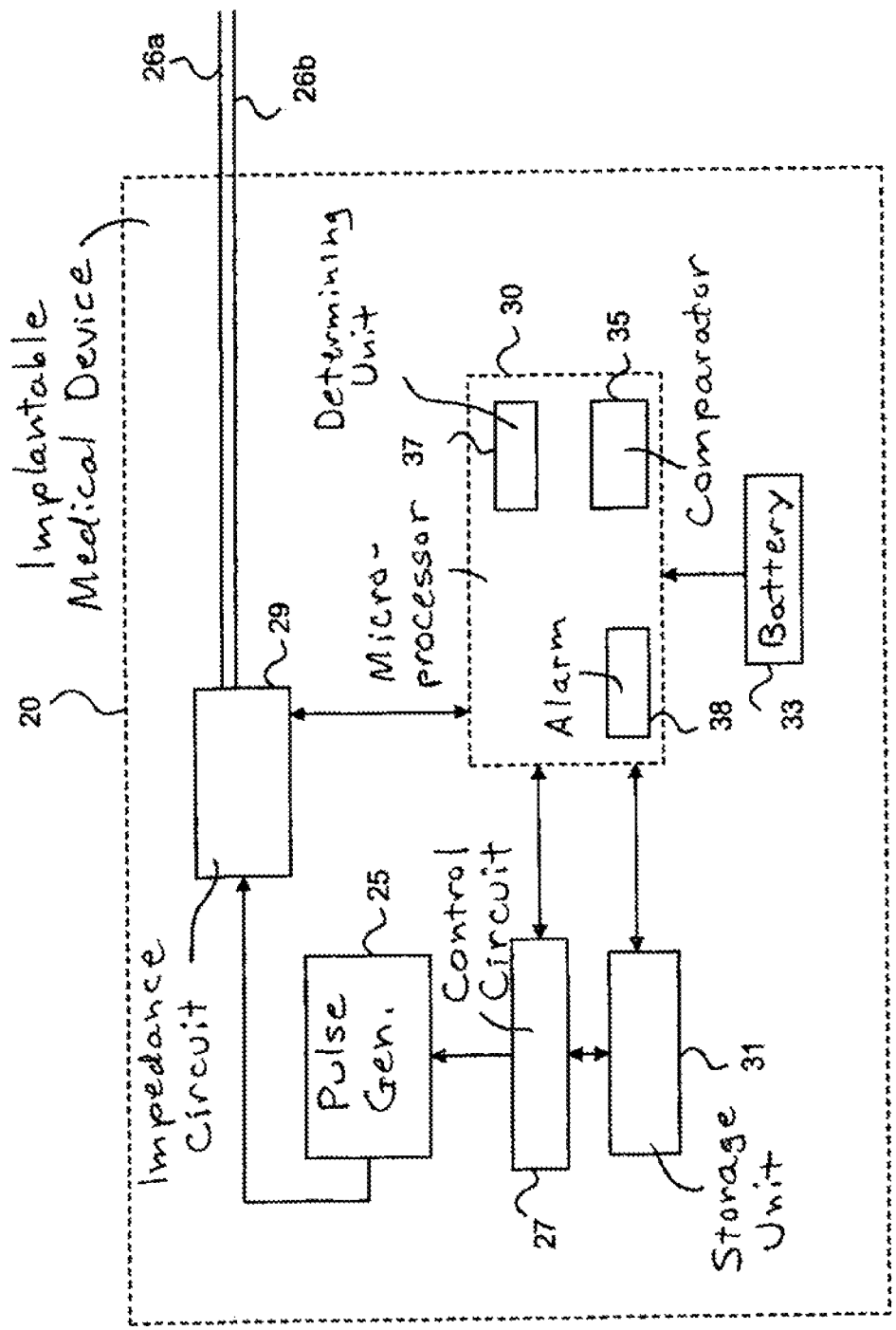
FIG. 2 is block diagram of the primary functional components of a first embodiment of the medical device according to the present invention.

FIG. 1 is a schematic diagram of a medical device implanted in a patient in which device the present invention can be implemented. This embodiment of the present invention is shown in the context of a pacemaker 2 implanted in a patient (not shown). The pacemaker 2 has a housing that is hermetically sealed and biologically inert. Normally, the housing is conductive and may thus serve as an electrode. One or more pacemaker leads, where only two are shown in FIG. 1 namely a ventricular lead 6a and an atrial lead 6b, are electrically coupled to the pacemaker 2 in a conventional manner. The leads 6a, 6b extend into the heart 8 via a vein 10 of the patient. One or more conductive electrodes for receiving electrical cardiac signals and/or for delivering electrical pacing to the heart 8 are arranged near the distal ends of the leads 6a, 6b. As the skilled man in the art realizes, the leads 6a, 6b may be implanted with its distal end located in either the atrium or ventricle of the heart 8, or in the coronary sinus or in the great cardiac vein, or they may be in form of epicardial leads attached directly at the epicardium With reference to FIG. 2, the configuration including the primary components of an embodiment of the present invention will be described. The illustrated embodiment includes an implantable medical device 20, such as the pacemaker shown in FIG. 1, and leads 26a and 26b, of the same type as the leads 6a and 6b shown in FIG. 1. The leads 26a, 26b may be unipolar or bipolar, and may include any of the passive or active fixation means known in the art for fixation of the lead to the cardiac tissue. As an example, the lead distal tip (not shown) may include a tined tip or a fixation helix. The leads 26a, 26b comprises one or more electrodes (as described with reference to FIG. 1), such as a tip electrode or a ring electrode, arranged to, inter alia, measure the impedance or transmit pacing pulses for causing depolarization of cardiac tissue adjacent to the electrode(-s) generated by a pace pulse generator 25 under influence of a control circuit 27. Preferably, the medical device 20 is connectable to the patient by means of a number of different electrode configurations including RV-tip (i.e. the distal electrode in a bipolar lead located in right ventricle) and RV-ring (i.e. the proximal electrode in a bipolar lead located in right ventricle), LV-tip (i.e. the distal electrode in a bipolar lead located in left ventricle) and RV tip (i.e. the distal electrode in a bipolar lead located in right ventricle), LV-tip (i.e. the distal electrode in a bipolar lead located in left ventricle) and RA-tip (i.e. the distal electrode in a bipolar lead located in right atrium), VC-tip (i.e. the distal electrode in a bipolar lead located in vena cava) and RA-tip (i.e. a distal electrode in a bipolar lead located in right atrium), or RA-tip (i.e. a distal electrode in a bipolar lead located in right atrium) and RV-tip (i.e. a distal electrode in a bipolar lead located in right ventricle) for excitation currents and RV-tip (i.e. the distal electrode in a bipolar lead located in right ventricle) and RV-ring (i.e. the proximal electrode in a bipolar lead located in right ventricle), LV-ring (i.e. the proximal electrode in a bipolar lead located in left ventricle) and RV-ring (i.e. the proximal electrode in a bipolar lead located in right ventricle), LV-ring (i.e. the proximal electrode in a bipolar lead located in left ventricle) and RA-ring (i.e. the proximal electrode in a bipolar lead located in right atrium), VC-coil (i.e. the conductor in a bipolar lead having a helical configuration located in vena cava) and RA-ring (i.e. the proximal electrode in a bipolar lead located in right atrium), or RA-ring (i.e. the proximal electrode in a bipolar lead located in right atrium) and RV-ring (i.e. the proximal electrode in a bipolar lead located in right ventricle) for voltages. Of course there are other configurations that can be used.

The control circuit 27 controls pace pulse parameters such as output voltage and pulse duration. Moreover, an impedance circuit 29 is arranged to carry out the impedance measurements. The impedance circuit 29 is arranged to apply the excitation current pulses between a first electrode of the above mentioned electrode configurations and second electrode of the configurations. The impedance circuit 29 is also arranged to measure the impedance in the tissues between the first and second electrode to the excitation current pulse of the configuration. Further, the impedance circuit 29 is coupled to a microprocessor 30, where processing of the measured impedance values can be performed. In an embodiment where the cardiac component of the electrical bio-impedance is measured, the impedance circuit 29 is arranged to apply an excitation current pulse between a first electrode and a second electrode arranged within the heart of the patient and to measure the impedance in the tissues between the first and second electrode to the excitation current pulse. By means of the different electrode configurations a number of different impedance measurements can be performed. For example, the excitation current can be measured between RV-tip and RV-ring, LV-tip and RV tip, LV-tip and RA-tip, VC-tip and RA-tip, or RA-tip and RV-tip, and, correspondingly, the voltage between RV-tip and RV-ring, LV-ring and RV-ring, LV-ring and RA-ring, VC-coil and RA-ring, or RA-ring and RV-ring. See above for definitions of the abbreviations. Of course, as the skilled man realizes, there are other conceivable configurations that can be used.

The impedance sensing circuit 29 is controlled by the microprocessor 30 and the control circuit 27. The control circuit 27 acts under influence of the microprocessor 30. A storage unit 31 is connected to the control circuit 27 and the microprocessor 30, which storage unit 31 may include a random access memory (RAM) and/or a non-volatile memory such as a read-only memory (ROM). The implantable medical device 20 is powered by a battery 33, which supplies electrical power to all electrical active components of the medical device 20. Data contained in the storage unit 31 can be transferred to a programmer (not shown) via a programmer interface (not shown) for use in analyzing system conditions, patient information, calculation of surrogate parameters such as systolic and diastolic slopes, the pre-ejection period, or left ventricular ejection time and changing pacing conditions, etc. Furthermore, data can be transferred from the programmer to the storage unit 31.

Measured impedance values are obtained by the microprocessor 30 from the impedance circuit 29 and stored in the storage unit 31. The microprocessor may be adapted to normalize the measured impedance values before they are used for posture determination. The medical device 20 further has a comparator 35 adapted to compare impedance values obtained by means of the impedance circuit 29 via one of, some of, or all of the above-mentioned electrode configurations with corresponding stored reference impedance values, which reference impedance values are stored in a reference value matrix in the storage unit 31. The reference impedance values may be created in a training session, which will be described in detail below, or may be obtained from a programmer as standard values.

Moreover, a determining unit 37 is adapted to determine a present posture of the patient by using the results from the comparison between the measured impedance values and corresponding stored reference impedance values. In a preferred embodiment, the comparator 35 and the determining unit 37 are integrated into the microprocessor 30. However, the comparator 35 and the determining unit 37 may also be implemented externally from the microprocessor 30 but connected to it. Furthermore, the comparator 35 and the determining unit 37 may be realized by software or hardware.

The medical device 20 may also include an alarm 38 adapted to send an updating indication signal indicating that the reference impedance values require an updating if a posture have not been determined in a patient posture determining session during a predetermined period of time. That is, the microprocessor 30 monitors whether a posture is detected in each posture determining session and if, if a posture have not been determined in a patient posture determining session during a predetermined period of time, it sends a triggering command to the alarm 38. The alarm 38 may be a vibrator causing the device to vibrate or it may be adapted to deliver a beeping sound in order to alert the patient of the situation. Furthermore, an alarm signal can, for example, also or instead be sent to the programmer (not shown) via the programmer interface (not shown). In a preferred embodiment, the alarm 38 is integrated into the microprocessor 30.

Figure 4:
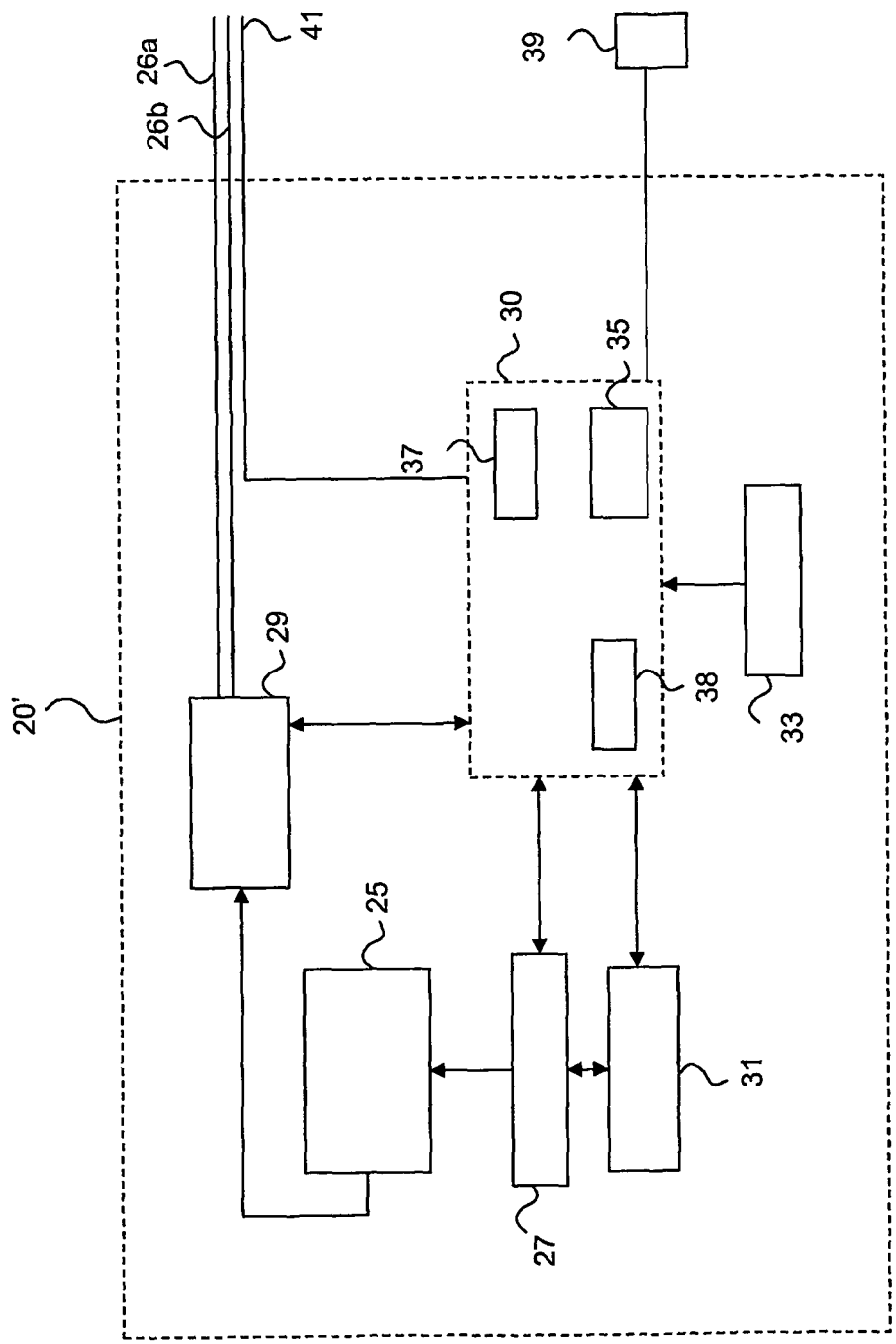
FIG. 4 is block diagram of the primary functional components of a further embodiment of the medical device according to the present invention.

According to an embodiment of the present invention, see FIG. 4, the medical device 20' includes a sensor 39 that senses the breathing rate of the patient connected to the microprocessor 30. The breathing rate sensor 39 can be adapted to filtering the impedance signal values by means of a band-pass filter adapted to the breathing rate.

The impedance measurement sessions can be executed over a predetermined number of breaths, and the impedance values can be calculated as a mean value over a predetermined number of breaths in accordance with:

$$\text{DC\_impedance\_level} = \frac{1}{k}\sum_{n=1}^{k} Z0(n) \qquad \text{(eq. 1)}$$

Alternatively, the reference impedance values are calculated as mean values of the measured impedance signal over a predetermined number of breathing cycles according to equation 1, for example, 2-10 cycles. In yet another embodiment, each reference value is calculated as a mean value of the measured impedance signal over a predetermined period of time, for example, about 16 seconds.

The medical device 20' may also include a heart rate sensor 41 connected to the microprocessor 30. The microprocessor 30 is adapted to determine whether the sensed heart rate is within a predetermined heart rate interval, for example, a heart rate between 60-90. If it is found that the sensed heart rate is within the predetermined heart rate interval, the microprocessor 30 is adapted to bring the impedance circuit 29 to initiate a patient posture determining session.

Figure 5:
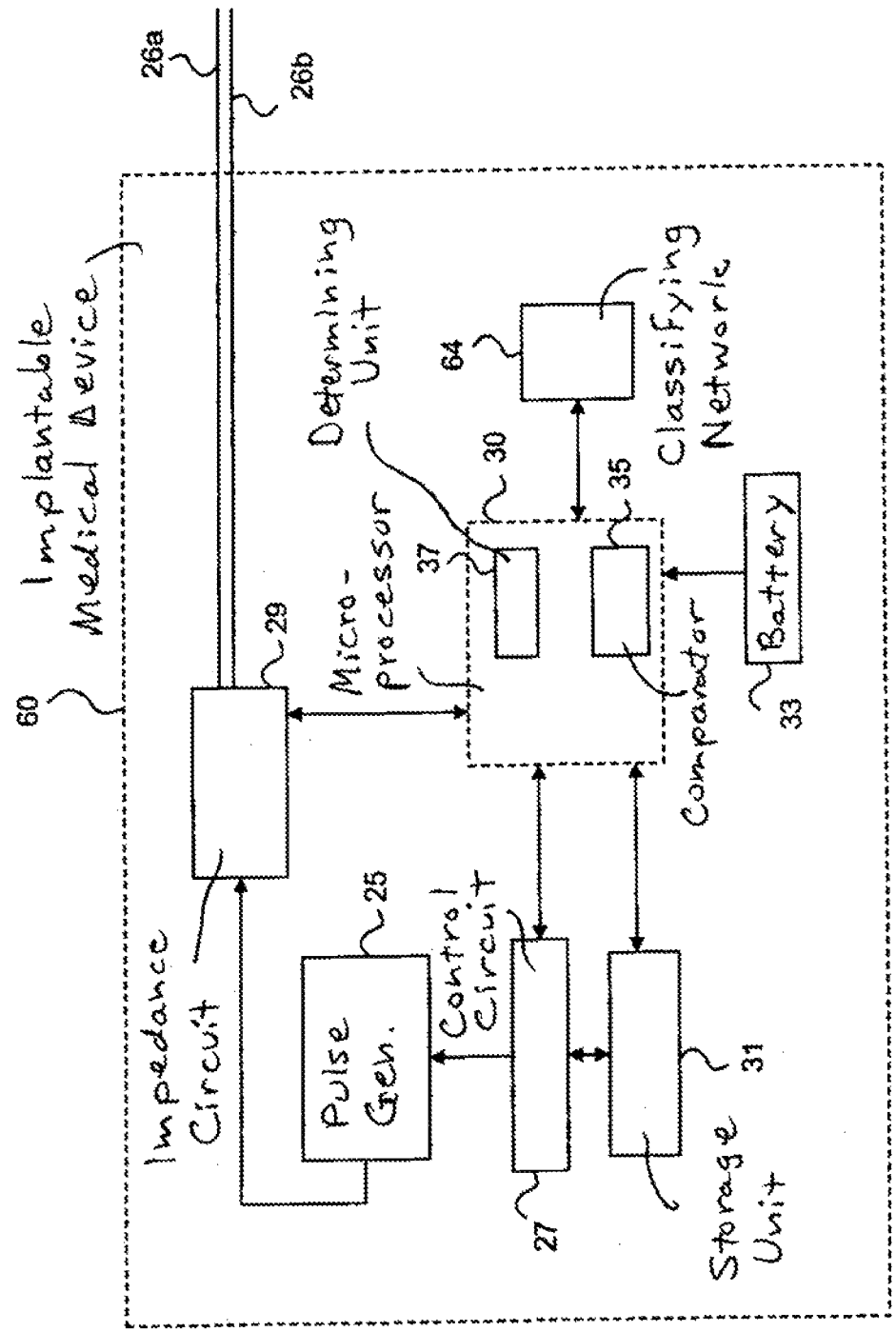
FIG. 5 is block diagram of the primary functional components of another embodiment of the medical device according to the present invention.

Furthermore, as shown in FIG. 5, the medical device 20' may include an activity sensor 43 that senses the activity level of the patient. The microprocessor 30 is adapted to determine whether the sensed activity level is below a predetermined activity level, for example, an activity lower than slow walk. If it is found that the sensed activity level is within the predetermined activity level interval, the microprocessor 30 is adapted to bring the impedance circuit 29 to initiate a patient posture determining session.

In addition, the medical device 20' may include sensor 45 that senses the body temperature of the patient, for example, a thermistor or other temperature sensor located in the vicinity of the heart connected to the microprocessor 30. The microprocessor 30 is adapted to determine whether the temperature is within a predetermined temperature level interval, for example, a temperature within the interval 36.5-37.5° C. and bring the impedance circuit 29 to initiate the patient posture determining session if the sensed body temperature is within said predetermined temperature level interval.

According to a further embodiment, the medical device 20 may include an arrangement that senses signals related to heart pumping activity of the patient (not shown) connected to the microprocessor 30, which may be adapted to determine the cardiac output based on the obtained signals, to determine whether the cardiac output is within a predetermined cardiac output level interval, and to bring the impedance circuit 29 to initiate the patient posture determining session if the sensed cardiac output is within the predetermined cardiac output level interval.

One, some or all of the breathing rate sensor 39, the heart rate sensor 41, the activity level sensor 43, the temperature sensor 45, or the arrangement for sensing signals related to heart pumping activity of the patient may be included in the medical device. That is, criteria from one, some, or all of those items can be combined in order to find appropriate conditions for initiating the patient posture determining session.

The reference value matrix discussed above, contains reference DC-level impedance values for a number of electrode configurations and for a number of different postures of the patient. An example of such a matrix is shown below in table 1. As can be seen, the matrix contains reference values for the electrode configurations config 1 to config x for the postures supine, prone, sitting, and standing. There are other postures than can be included, for example, lying on the right side or the left side.

TABLE 1

| Posture | Config 1 | Config 2 | Config 3 | Config x |
|---|---|---|---|---|
| Supine | S1 | S2 | S3 | Sx |
| Prone | P1 | P2 | P3 | Px |
| Sitting | Si1 | Si2 | Si3 | Six |
| Standing | St1 | St2 | St3 | Stx |

As discussed above, the impedance is very posture sensitive and pre-clinical trials on sheep have shown that the DC-level of the impedance may vary 25-40% depending on the subject's position. This is true for both the DC-impedance measured over the lungs (e.g. between the case of the device and an electrode within the heart) and for the DC-impedance measured within the heart (e.g. the RV-RA or RV-LV). Hence, the reference values shown in table 1 will vary significantly between different postures for an electrode configuration and between different configurations for the same posture.

According to a preferred embodiment, these reference values S1, S2, ..., Stx are created during a training session. For example, this session can be performed at a doctors office, where the patient is located in the four positions and an impedance measurement sessions is performed for each configuration Config 1 to Config x in each position. That is, the patient is first instructed to position his or her body in the first posture, for example, supine. Then, an impedance measurement session is initiated in a first electrode configuration, for example, RV-tip-RV-ring for the excitation current and RV-tip-RV-ring for the voltage in order to measure the reference impedance values for the first configuration. Thereafter, an impedance measurement session is initiated in a second electrode configuration, for example, LV-tip-RV-tip for the excitation current and LV-ring-RV-ring for the voltage in order to measure the reference impedance values for the second configuration. This will be repeated for all electrode configurations. After the reference impedance values has been measured for each electrode configuration for the first posture, in this exempla supine, the patient is instructed the change his or her posture to the following, in this example, prone. Thereafter, the procedure is repeated in accordance with the above given description. Accordingly, the medical device is provided with reference impedance values customized for the specific patient, thereby increasing the accuracy and reliability of the position determination.

The measured impedance values are stored in the reference value matrix. Preferably, each impedance value is calculated as the mean value of the impedance signal over a predetermined number of breaths in accordance with equation 1, see above.

Alternatively, the reference impedance values are calculated as mean values of the measured impedance signal over a predetermined number of breathing cycles according to equation 1, for example, 2-10 cycles. In yet another embodiment, each reference value is calculated as a mean value of the measured impedance signal over a predetermined period of time, for example, about 16 seconds.

According to a preferred embodiment of the present invention, the reference DC impedance values (S1 ... Sx, P1 ... Px, Si1 ... Six, St1 ... Stx) are normalized, which is performed within each DC impedance configuration. In a first alternative normalization procedure, each reference value is normalized with the sum of all the impedance values of the configuration according to the following:

$$S1norm = S1/Z1norm, Z1norm = (S1 + P1 + Si1 + St1);$$

$$S2norm = S2/Z2norm, Z2norm = (S2 + P2 + Si2 + St2);$$

$$\vdots$$

$$St3norm = St3/Zt3norm, Zt3norm = (S3 + P3 + Si3 + St3);$$

and $$Stxnorm = Stx/Ztxnorm, Ztxnorm = (Sx, Px, Six, Stx);$$

That is, each configuration is normalized such that the sum of the normalized DC impedance reference values for each configuration is 1.

In another alternative normalization procedure the measurements for each configuration is divided with the largest DC impedance value in the configuration according to the following:

$$S1norm = S1/Z1norm, Z1norm = \max(S1 + P1 + Si1 + St1);$$

$$S2norm = S2/Z2norm, Z2norm = \max(S2 + P2 + Si2 + St2);$$

$$\vdots$$

$$St3norm = St3/Zt3norm, Zt3norm = \max(S3 + P3 + Si3 + St3);$$

and $$Stxnorm = Stx/Ztxnorm, Ztxnorm = \max(Sx, Px, Six, Stx)$$

Thus, irrespective which normalization procedure being used, the reference matrix will now contain normalized reference values for the electrode configurations config 1 to config x for the postures supine, prone, sitting, and standing.

TABLE 2

| Posture | Config 1 | Config 2 | Config 3 | Config x |
|---|---|---|---|---|
| Supine | S1norm | S2norm | S3norm | Sxnorm |
| Prone | P1norm | P2norm | P3norm | Pxnorm |
| Sitting | Si1norm | Si2norm | Si3norm | Sixnorm |
| Standing | St1norm | St2norm | St3norm | Stxnorm |
| Norm. factor | Z1norm | Z2norm | Z3norm | Z4norm |

At initiation of the training session for finding the reference values, a configuration verification procedure is performed in order to check whether a specific configuration is qualified. That is, whether a specific configuration suitable to use. According to a first embodiment, this is performed in accordance with the following. The examples disclosed hereinafter are described with reference to the normalized values, but, as the skilled man realize, the non-normalized values can of course be used instead. First, it is checked that the difference between the DC impedance values for different postures are larger that a predetermined value Q. This predetermined value Q can be programmed in advance to the training sessions or can be determined manually at initiating of the procedure. Hence, the following check is performed for each configuration y:

$$\text{Min}(|Synorm-Pynorm|,|Synorm-Siynorm|,|Synorm-Stynorm|,\ldots,|Stynorm-Siynorm|) > Q \quad \text{(eqt. 2)}$$

According to an alternative procedure, the sum of all differences is calculated and, thereafter, it is checked whether the sum is larger than a predetermined value R. This predetermined value R can be programmed in advance to the training sessions or can be determined manually at initiation of the procedure. Hence, the following check is performed for each configuration y:

$$\text{sum}(|Synorm-Pynorm|,|Synorm-Siynorm|,|Synorm-Stynorm|,\ldots,|Stynorm-Siynorm|) > R \quad \text{(eqt. 3)}$$

If the condition in either equation 2 or 3 is not satisfied, the specific configuration is judged not to discriminate different postures of the patient in a sufficient way and should therefore be excluded from use when determining a posture of the patient.

According to further embodiments, an identifying procedure is performed during the training session in order to identify which configurations that should be used in combination with each other to provide a sufficient separation between DC impedance reference values from each other for the different postures. In one embodiment, two configurations are checked first and the squared difference is calculated for each posture's DC impedance reference values into the other postures in accordance with the following:

$$\text{MSE\_SP\_false} = \left(S1norm - \frac{P1}{Z1norm}\right)^2 + \left(S2norm - \frac{P2}{Z2norm}\right)^2$$

$$\text{MSE\_SiP\_false} = \left(Si1norm - \frac{P1}{Z1norm}\right)^2 + \left(Si2norm - \frac{P2}{Z2norm}\right)^2$$

$$\vdots$$

$$\text{MSE\_SSt\_false} = \left(S1norm - \frac{St1}{Z1norm}\right)^2 + \left(S2norm - \frac{St2}{Z2norm}\right)^2$$

$$\vdots$$

If all MSE_false values are larger than a predetermined value (which may be programmable), the two configurations are considered to be sufficient. If not all MSE_false values are larger than the predetermined value, two other configurations are tested. This is repeated until either a combination being good enough has been identified or all combinations have been tested. If all combination of two configurations has been tested without identifying a suitable combination, the above mentioned MSE_false values are calculated for three configurations instead of for two. This is repeated until either a combination (of three configurations) being good enough has been identified or all combinations have been tested. The above-mentioned procedure can be repeated for four, five combinations and so on until a suitable combination of configurations is found.

According to an alternative embodiment, the MSE_false values are calculated in accordance with the description above, but the procedure starts with all configurations and then removes one configuration at a time and checks the impact on the MSE_false values. For example, in the example described above with reference to table 1 and 2, the procedure starts with 4 configurations and one configuration is removed and the MSE_false values are calculated. This is repeated for all four configurations, i.e. each of the four configurations is removed one at a time and the MSE_false is calculated. The configuration having the least impact on the MSE_false values is determined to be the least important configuration and is removed from the test. This is then repeated for the three remaining configurations and so on.

Instead of performing a training session as described above, impedance reference values can be obtained from a look-up table containing standard values, which may be normalized in accordance with the above given description. For example, these standard values can be transferred to the device 20 wirelessly from a programmer.

Figure 3:
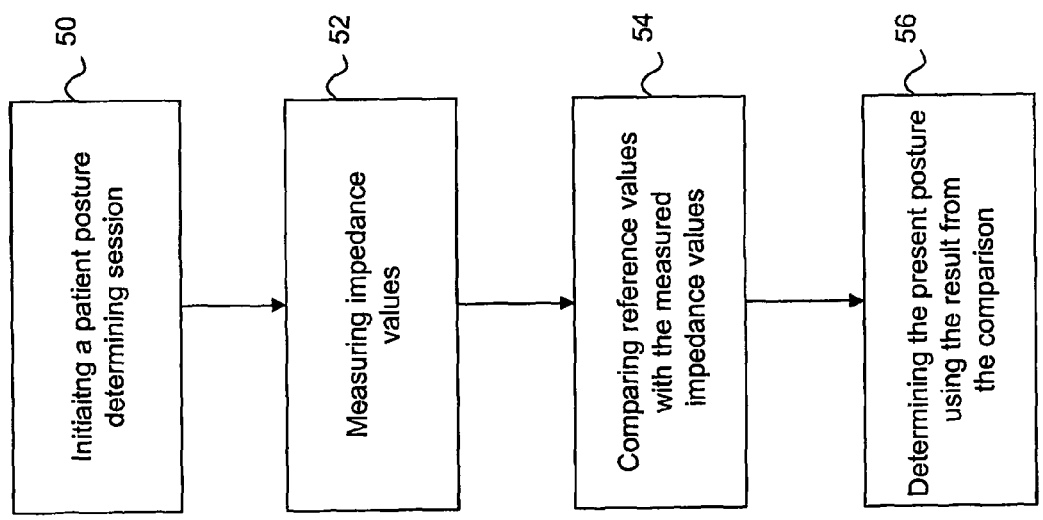
FIG. 3 is a flow chart illustrating the steps in accordance with one embodiment of the present invention for determining the posture of a patient.

Referring now to FIG. 3, a high-level description of the method for determining the posture of a patient according to the present invention will be given. First, at step 50, a patient posture determining session is initiated by performing an electrical bio-impedance measurement session in the different electrode configurations in order to measure an impedance value for the configuration. Preferably, impedance measurement sessions are initiated in several configurations and the microprocessor 30 is adapted to send a control instruction to the impedance circuit 29 containing information regarding which electrode configuration that is to be used in, if several are utilized, in which order they should be used. Preferably, each impedance value is calculated as the mean value of the impedance signal over a predetermined number of breaths in accordance with equation 1. Alternatively, the reference impedance values are calculated as mean values of the measured impedance signal over a predetermined number of breathing cycles according to equation 1, for example, 2-10 cycles. In yet another embodiment, each reference value is calculated as a mean value of the measured impedance signal over a predetermined period of time, for example, about 16 seconds. The measured impedance values for the x used configurations newZ1, newZ2, newZ3, newZx are then stored temporarily in storage means 31.

Thereafter, at step 52, the corresponding reference impedance values, shown in table 1 or table 2, for the postures supine, prone, sitting and standing are collected from the reference matrix in the storage unit together with the present impedance values. Then, at step 54, the measured impedance values are compared in the comparing means 35 with corresponding reference impedance values. A deviation factor is determined for each position and according to a preferred embodiment, the square error sum for each potential position or posture is calculated in accordance with the following equations 4-7:

$$MSE\_S = \left(\frac{S1-newZ1}{S1}\right)^2 + \left(\frac{S2-newZ2}{S2}\right)^2 + \ldots + \left(\frac{Sx-newZx}{Sx}\right)^2 \quad \text{(eqt. 4)}$$

$$MSE\_P = \left(\frac{P1-newZ1}{P1}\right)^2 + \left(\frac{P2-newZ2}{P2}\right)^2 + \ldots + \left(\frac{Px-newZx}{Px}\right)^2 \quad \text{(eqt. 5)}$$

$$MSE\_Si = \left(\frac{Si1-newZ1}{Si1}\right)^2 + \left(\frac{Si2-newZ2}{Si2}\right)^2 + \ldots + \left(\frac{Six-newZx}{Six}\right)^2 \quad \text{(eqt. 6)}$$

$$MSE\_St = \left(\frac{St1-newZ1}{St1}\right)^2 + \left(\frac{St2-newZ2}{St2}\right)^2 + \ldots + \left(\frac{Stx-newZx}{Stx}\right)^2 \quad \text{(eqt. 7)}$$

If, instead the normalized values found in table 2, the deviation factor is determined for each position in accordance with the following equations 8-11:

$$MSE\_S = \left(S1norm - \frac{newZ1}{Z1norm}\right)^2 + \left(S2norm - \frac{newZ2}{Z2norm}\right)^2 + \ldots + \left(Sxnorm - \frac{newZx}{Zxnorm}\right)^2 \quad \text{(eqt. 8)}$$

$$MSE\_P = \left(P1norm - \frac{newZ1}{Z1norm}\right)^2 + \left(P2norm - \frac{newZ2}{Z2norm}\right)^2 + \ldots + \left(Pxnorm - \frac{newZx}{Zxnorm}\right)^2 \quad \text{(eqt. 9)}$$

$$MSE\_Si = \left(Si1 - \frac{newZ1}{Z1norm}\right)^2 + \left(Si2 - \frac{newZ2}{Z2norm}\right)^2 + \ldots + \left(Sxnorm - \frac{newZx}{Zxnorm}\right)^2 \quad \text{(eqt. 10)}$$

$$MSE\_St = \left(St1norm - \frac{newZ1}{Z1norm}\right)^2 + \left(St2norm - \frac{newZ2}{St2}\right)^2 + \ldots + \left(Stxnorm - \frac{newZx}{Stx}\right)^2 \quad \text{(eqt. 11)}$$

Finally, at step 56, the present posture of the patient is determined in the determining unit 37 by using the results from the comparison between measured impedance values and the stored reference impedance values and the subject, i.e. the patient, is determined to be in the position having the lowest squared error sum. In the preferred embodiment, where the squared difference sum for each potential position or posture was calculated, the patient is determined to be in the position or posture that has the lowest squared difference sum.

In another embodiment of the present invention, an interval or range is set for each reference value. During the comparison procedure is checked whether each respective measured impedance value is within the interval for each respective reference value of each potential posture. The potential posture where all measured impedance values is within respective interval is determined to be the present posture of the patient.

According to yet another embodiment of the present invention, the sum of the differences is calculated according to the following equations 12-15:

$$SUM\_S = S1-newZ1+S2-newZ2+S3-newZ3+\ldots +Sx-newZx \quad \text{(eqt. 12)}$$

$$SUM\_P = P1-newZ1+P2-newZ2+P3-newZ3+\ldots +Px-newZx \quad \text{(eqt. 13)}$$

$$SUM\_Si = Si1-newZ1+Si2-newZ2+Si3-newZ3+\ldots +Six-newZx \quad \text{(eqt. 14)}$$

$$SUM\_St = St1-newZ1+St2-newZ2+St3-newZ3+\ldots +Stx-newZx \quad \text{(eqt. 15)}$$

The potential posture having the lowest total sum is then determined to be the actual posture of the patient. Of course, these sums can also be normalized.

Figure 6:
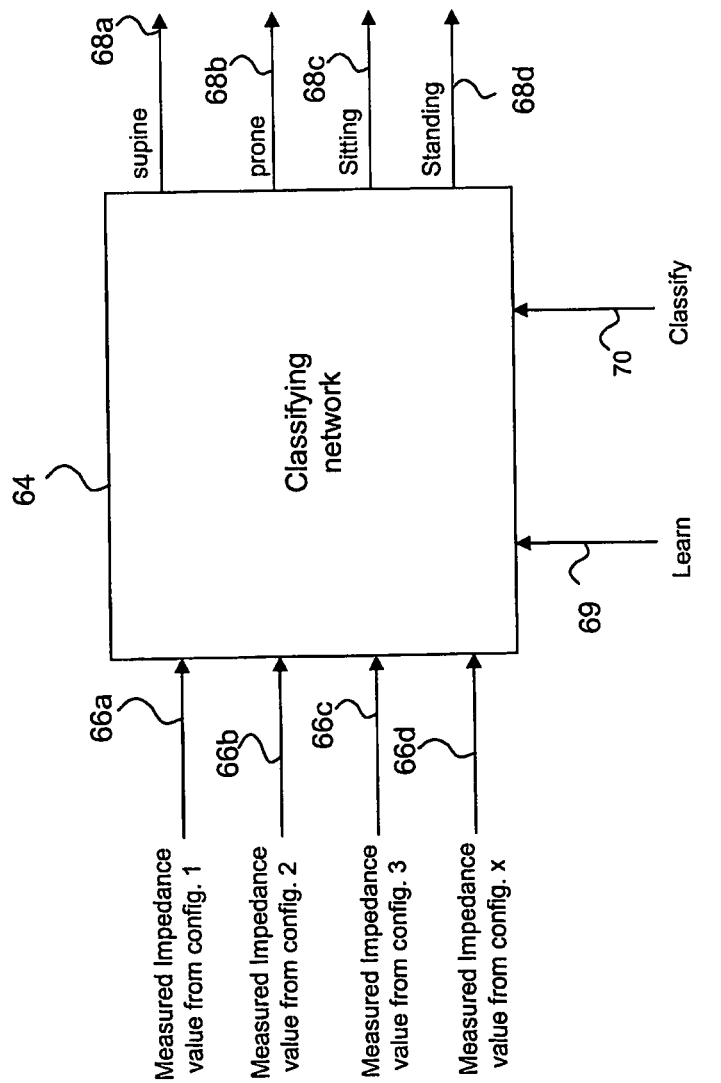
FIG. 6 is a schematic diagram showing a classifying network in accordance with the present invention.

With reference now to FIGS. 5, 6, 7a and 7b, a further embodiment of the present invention will be discussed. Turning first to FIG. 5, the medical device according to this embodiment will be described, where parts and/or means similar to parts and/or means shown in FIGS. 2 and 4 will be denoted with the same reference numerals and the description thereof will be omitted in the following. The medical device 60 comprises a classifying network 64, which utilizes a neural network or a fuzzy logic structure. The design and general function of a neural network or a fuzzy logic classifying network is well known for the man skilled within the art and descriptions thereof are, therefore, omitted. During the training session, measured impedance values from the different electrode configurations are obtained by the microprocessor 30 from the impedance measurement means 29, stored in the storage means 31, and normalized in the processor 30. The classifying network 64 is adapted to operate in a learning mode and in a classifying mode. In the learning mode the classifying network 64 is trained to recognize a known or specific body posture and in the classifying mode the network 64 identifies a body posture by means of measured impedance values obtained during a body posture determining session. The output of the classifying network is preferably binary and a logical 1 may indicate a classified body posture other outputs are at a logical 0. In FIG. 6, a schematic diagram of such a classifying network in shown. It should be noted that such a network can be implemented in software as well as in hardware, as shown in FIGS. 5 and 6. As can be seen, the classifying network 64 is adapted to receive a vector containing the normalized impedance values from the different configurations config. 1, config. 2, config. 3 and config. x at respective inputs 66a-66d. In addition, the network 64 is adapted to output binary outputs at outputs 68a-68d in terms of classified body posture supine, prone, sitting or standing, respectively. Furthermore, the network 64 is adapted to receive, via input 69, a learning mode activation signal from the processor 30 activating the learn mode of the network 64, and, via input 70, a classifying mode activation signal from the processor 30 activating the classifying mode.

Figure 7A:
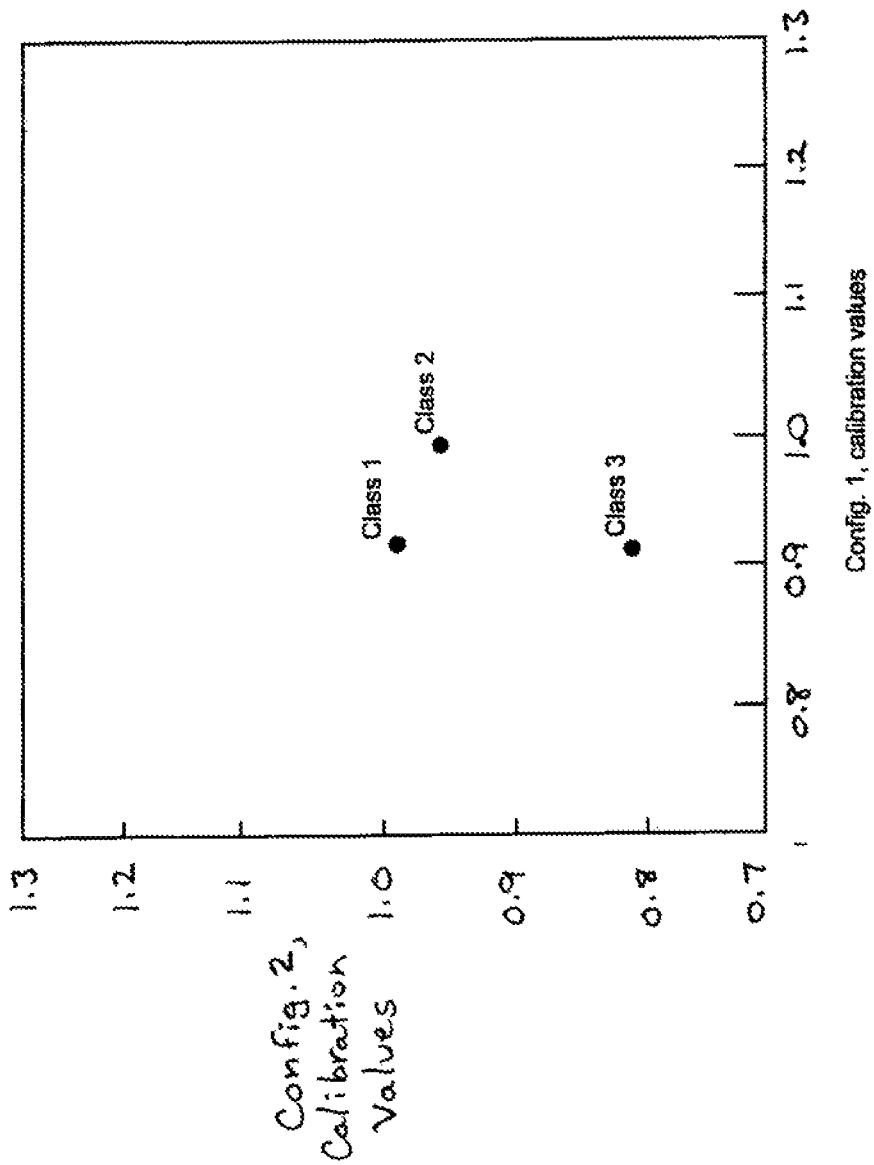
FIG. 7a is a diagram showing the normalized impedance value vectors and their associated body postures used in a neural network in accordance with the present invention.
Figure 7B:
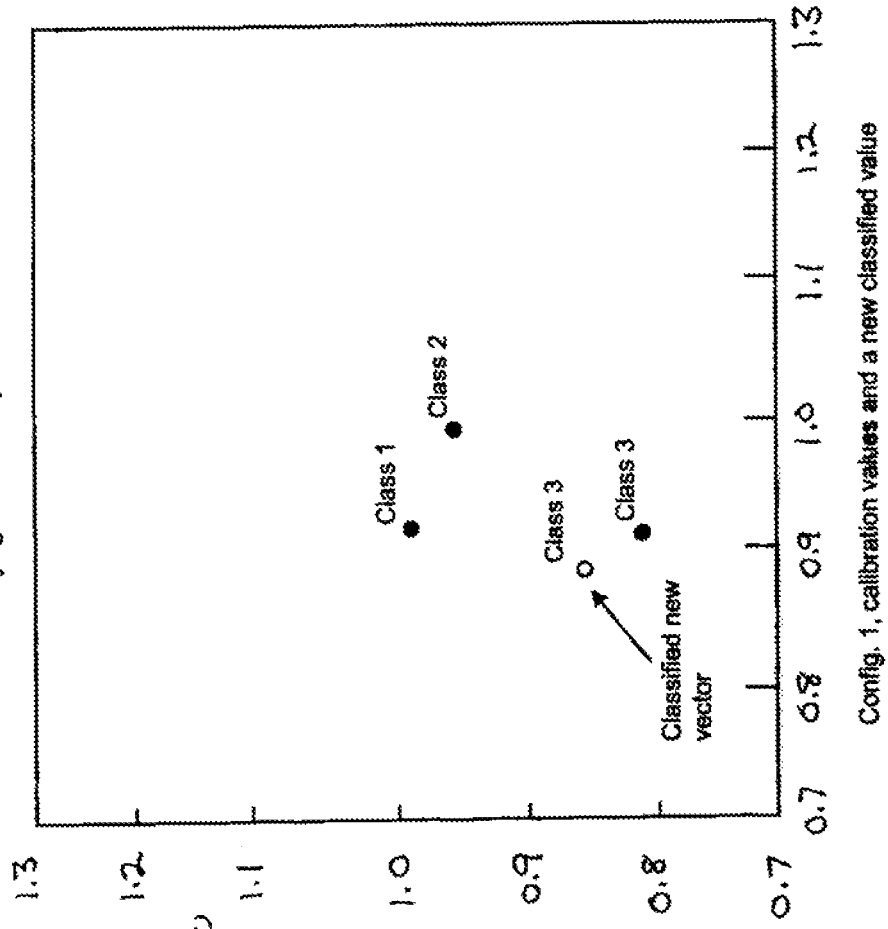
FIG. 7b is a diagram showing the classifying of a new impedance value vector in a neural network in accordance with the present invention.

Hereinafter, an illustrating example of the function of the network 64, for example, a probalistic neural network will be discussed with reference to FIGS. 7a and 7b, respectively. In this illustrative example, only two configurations are used to discriminate between three different positions or postures, but, of course, an arbitrary number of electrode configurations can be used and there are also a large number of other postures that are of interest to identify in addition to the above-mentioned.

During the training session, which may take place in a doctors office as outlined above, the following set of impedance values is obtained (measured in ohms), see table 3.

TABLE 3

| Posture | Config. 1 (Ohms) | Config. 2 (Ohms) | Target class |
|---------|------------------|------------------|--------------|
| Supine | 706 | 410 | 1 |
| Left side | 748 | 386 | 2 |
| Prone | 687 | 326 | 3 |

The measure impedance values are normalized, for example, to the maximum impedance value of respective configuration and the normalized values will have a value in the range 0 to 1, see table 4 below.

TABLE 4

| Posture | Config. 1 | Config. 2 | Target class |
|---------|-----------|-----------|--------------|
| Supine | 0.9439 | 1 | 1 |
| Left side | 1 | 0.9415 | 2 |
| Prone | 0.9184 | 0.7951 | 3 |

The training set, shown in table 4, is then used to train the network to the three output target classes 1, 2, and 3 in accordance with conventional practice within the art. Preferably, the output is coded as a binary one of P code, where P is the number of classified body postures, see table 5 below.

TABLE 5

| Posture | Config. 1 | Config. 2 | Target class | Binary code |
|---------|-----------|-----------|--------------|-------------|
| Supine | 0.9439 | 1 | 1 | 0 0 1 |
| Left side | 1 | 0.9415 | 2 | 0 1 0 |
| Prone | 0.9184 | 0.7951 | 3 | 1 0 0 |

Thus, for example, a binary output of 0 0 1 will indicate that the patient is in supine. This is convenient, for example, in a situation where a certain body posture has to be identified for measurement of a physical parameter by the implanted device, e.g. measurement of the pre-ejection period in the supine body posture using an implantable pressure sensor. In FIG. 7a, a schematic diagram illustrating the three normalized impedance value vectors of table 4 and 5, i.e. the calibration values, and their associated body postures in the learning mode is shown. At a body posture determining session, the classifying mode, as described above, is initiated. The new measured impedance value vector is normalized and compared with the calibration values as shown in FIG. 7b. As can be seen in this example, the new classified impedance value vector is positioned as indicated in FIG. 7b and the body posture is accordingly classified to be prone. The classifying is performed by assuming that the present position is the position being closest to the measured impedance value vector in FIG. 7b.

Although modifications and changes may be suggested by those skilled in the art, it is the intention of the inventors to embody within the patent warranted heron all changes and modifications as reasonably and properly come within the scope of their contribution to the art.

The invention claimed is:

1. A method for determining the posture of a patient comprising the steps of:
   with a bio-impedance measurement device having a plurality of electrodes configured to interact with the patient in a plurality of different electrode configurations, initiating a patient posture determining session by measuring an impedance value of the patient with said electrodes in at least one configuration among said plurality of configurations;
   selecting a reference impedance value from among a plurality of stored reference impedance values for said at least one configuration, said plurality of stored reference impedance values being respectively associated with different postures of the patient, and the posture associated with the selected reference impedance value representing a candidate posture;
   comparing the measured impedance value with the selected reference impedance value, thereby obtaining a comparison result; and
   dependent on said comparison result, automatically electronically determining whether the current posture of the patient conforms to the candidate posture.

2. A method as claimed in claim 1 comprising:
   obtaining said reference impedance values for each of a predetermined number of said electrode configurations for each of a predetermined number of different postures for each of a predetermined number of said electrode configurations; and
   storing the reference impedance values in a reference value matrix representing each reference impedance value associated with each electrode configuration and each posture.

3. A method as claimed in claim 2 comprising:
   sensing a breathing rate of the patient; and
   determining said impedance value as an average value over a duration selected from the group consisting of a predetermined number of breaths, a predetermined number of breathing cycles, and a predetermined period of time.

4. A method as claimed in claim 3 comprising synchronizing the respective impedance measurement sessions with said breathing rate.

5. A method as claimed in claim 1 comprising:
   automatically determining whether a difference between said measured impedance value for said at least one configuration and the reference value for said at least one configuration is within a predetermined interval; and
   if said difference is outside of said interval for a predetermined number of posture determining sessions, updating the stored reference impedance values by using the measure impedance value of said predetermined number of posture determining sessions.

6. A method as claimed in claim 1 wherein the step of comparing said measured impedance value with said stored reference impedance value comprises calculating a deviation factor, as said comparison result, for the posture associated with said reference impedance value, and determining whether said current posture conforms to said candidate posture using said deviation factor.

7. A method as claimed in claim 6 comprising calculating said deviation factor as a squared difference sum of said measured impedance values and stored reference impedance value for said candidate posture.

8. A method as claimed in claim 7 comprising identifying a candidate posture, among said postures respectively associated with the stored reference impedance values, having a lowest squared difference sum and determining said current posture as being said candidate posture having said lowest squared difference sum.

9. A method as claimed in claim 7 comprising determining whether said squared difference sum for said candidate posture is within a predetermined interval, and determining said current posture to be said candidate posture if said squared difference sum is within said predetermined interval.

10. A method as claimed in claim 1 comprising sensing a physiological feature of said patient selected from the group consisting of heart rate, activity level, body temperature and cardiac output, and initiating said patient posture determining session only when said physiological feature is at a predetermined level.

11. A method as claimed in claim 1 comprising generating an updating indication signal indicating that said reference impedance values require updating, if a current posture is not determined in said patient posture determining session within a predetermined period of time.

12. A device for determining the posture of a patient comprising the steps of:
a bio-impedance measurement device having a plurality of electrodes configured to interact with the patient in a plurality of different electrode configurations, that initiates a patient posture determining session by measuring an impedance value of the patient with said electrodes in at least one configuration among said plurality of configurations;
a memory containing for said at least one configuration, a plurality of stored reference impedance values respectively associated with different postures of the patient;
a processor that selects a reference impedance value from said memory, the posture associated with the selected reference impedance value representing a candidate posture;
said processor comprising a comparator that compares the measured impedance value with the selected reference impedance value to obtain a comparison result; and
said processor dependent on said comparison result, automatically determining whether the current posture of the patient conforms to the candidate posture.

13. A device as claimed in claim 12 wherein said memory contains reference impedance values for each of a predetermined number of said electrode configurations for each of a predetermined number of different postures for each of a predetermined number of said electrode configurations and wherein the reference impedance values are stored in the memory in a reference value matrix representing each reference impedance value associated with each electrode configuration and each posture.

14. A device as claimed in claim 13 comprising:
a breathing rate sensor that senses a breathing rate of the patient; and
wherein said processor determines said impedance value as an average value over a duration selected from the group consisting of a predetermined number of breaths, a predetermined number of breathing cycles, and a predetermined period of time.

15. A device as claimed in claim 14 comprising a control unit that synchronizes the respective impedance measurement sessions with said breathing rate.

16. A device as claimed in claim 12 wherein said processor automatically determines whether a difference between said measured impedance value for said at least one configuration and the reference value for said at least one configuration is within a predetermined interval and, if said difference is outside of said interval for a predetermined number of posture determining sessions, updates the stored reference impedance values by using the measure impedance value of said predetermined number of posture determining sessions.

17. A device as claimed in claim 12 wherein said comparator compares said measured impedance value with said stored reference impedance value by calculating a deviation factor, as said comparison result, for the posture associated with said reference impedance value, and wherein said processor determines whether said current posture conforms to said candidate posture using said deviation factor.

18. A device as claimed in claim 17 wherein said comparator calculates said deviation factor as a squared difference sum of said measured impedance values and stored reference impedance values for said candidate posture.

19. A device as claimed in claim 18 wherein said processor identifies a candidate posture, among said postures having a lowest squared difference sum and determining said current posture as being said candidate posture having said lowest squared difference sum.

20. A device as claimed in claim 18 wherein said processor determines whether said squared difference sum for said candidate posture is within a predetermined interval, and determines said current posture to be said candidate posture to said squared difference sum is within said predetermined interval.

21. A device as claimed in claim 12 comprising a sensing arrangement that detects a physiological feature of said patient selected from the group consisting of heart rate, activity level, body temperature and cardiac output, and comprising a control unit that initiates said patient posture determining session only when said physiological feature is at a predetermined level.

22. A device as claimed in claim 12 wherein said processor generates an updating indication signal indicating that said reference impedance values require updating, if a current posture is not determined in said patient posture determining session within a predetermined period of time.

23. A computer-readable medium encoded with programming instructions for determining the posture of a patient for use with a bio-impedance measurement device having a plurality of electrodes configured to interact with the patient in a plurality of different electrode configurations, said programming instructions causing a computerized circuit to:
operate said bio-impedance measurement device to initiate a patient posture determining session by measuring an impedance value of the patient with said electrodes in at least one configuration among said plurality of configurations;
select a reference impedance value from among a plurality of stored reference impedance values for said at least one configuration, said plurality of stored reference impedance values being respectively associated with different postures of the patient, and the posture associated with the selected reference impedance value representing a candidate posture;
compare the measured impedance value with the selected reference impedance value, thereby obtaining a comparison result; and
dependent on said comparison result, determine whether the current posture of the patient conforms to the candidate posture.

* * * * *